United States Patent [19] [11] 4,107,425
Pfeffer et al. [45] Aug. 15, 1978

[54] PREPARATION OF 1-α- AND 1-β-GLUCOSE ESTERS BY STEREOSELECTIVE ACYLATION OF METALATED 2,3,4,6,-TETRA-O-BENZYL-D-GLUCOPYRANOSE

[75] Inventors: Philip E. Pfeffer, Warrington; Gordon G. Moore, Willow Grove, both of Pa.

[73] Assignee: The United States of America as represented by the Secretary of Agriculture, Washington, D.C.

[21] Appl. No.: 768,916

[22] Filed: Feb. 15, 1977

[51] Int. Cl.² .................................... C07H 13/02
[52] U.S. Cl. ..................... 536/119; 536/4; 536/115; 536/121
[58] Field of Search .............. 536/4, 119, 121, 115

[56] References Cited
U.S. PATENT DOCUMENTS 1,994,608  3/1935  Hagedorn ...................... 536/119
3,756,966  9/1973  Lamberti ....................... 536/121
3,849,341  11/1974 Lamberti ....................... 536/119
3,981,860  9/1976  Szkrybalo ..................... 536/119

Primary Examiner—Johnnie R. Brown
Attorney, Agent, or Firm—M. Howard Silverstein; William E. Scott; David G. McConnell

[57] ABSTRACT

Anomerically pure 1-α- and 1-β-esters of 2,3,4,6-Tetra-O-benzyl-D-glucopyranose have been prepared in high yield by controlling the stereochemistry of 1-O-acylation of appropriately protected D-glucose. 2,3,4,6-tetra-O-benzyl-D-glucopyranose is metalated with n-butyllithium in either tetrahydrofuran or anhydrous benzene and the metalated product acylated with an appropriate alkyl, alkenyl, or aryl acid chloride. Hydrogenation of the acyl glucopyranose, when derived from a saturated acid chloride, yields the appropriate 1-α- or 1-β-D-glucose ester. Reaction in tetrahydrofuran produces the α-anomer while reaction in anhydrous benzene produces the β-anomer.

5 Claims, No Drawings

PREPARATION OF 1-α- AND 1-β-GLUCOSE ESTERS BY STEREOSELECTIVE ACYLATION OF METALATED 2,3,4,6,-TETRA-O-BENZYL-D-GLUCOPYRANOSE

BACKGROUND OF THE INVENTION

1. Field of the Invention

This invention relates to the successful controlling of the stereochemistry of 1-O-acylation of appropriately protected D-glucose to synthesize anomerically pure 1-α- and 1-β-esters of 2,3,4,6-tetra-O-benzyl-D-glucopyranose and anomerically pure 1-α- and 1-β-D-glucose esters.

2. Description of the Prior Art

The prior art does not provide any easy procedures for the preparation of glucosyl esters, especially the α-D-anomers. In fact, the only known examples are the gallate and the mesitoate which were made by indirect routes in low yields. The gallate was prepared in 5% yield by the procedure of Schmidt (Justus Liebigs Ann. Chem., 587, 63, 1954), and the mesitoate in 17% yield by the procedure of Fletcher (J. Am. Chem. Soc., 82, 3215, 1960). Such procedures for the preparation of 1-α-glucosyl esters were chosen because the hindered ester functions are less likely to rearrange, that is, migrate from position 1 to position 2, under the nonneutral deblocking conditions utilized. Furthermore, Fletcher could not extend either procedure to less hindered systems because of the lack of stereospecificity in the acylation procedure employed and loss of desired product through rapid migration of the unhindered ester function from C-1 to C-2 under the non-neutral deblocking conditions (J. Am Chem. Soc., 78, 2849, 1956).

BRIEF SUMMARY OF THE INVENTION

It is an object of this invention to provide a means of preparing in high yield pure 1-α- and 1-β-glucosyl esters.

Another object of this invention is to provide a means of successfully controlling the stereochemistry of 1-O-acylation of appropriately protected D-glucose to produce, selectively, the desired α- and β-acylated products.

A further object is to provide a means of successfully controlling the stereochemistry of 1-O-acylation of appropriately protected D-glucose to produce, selectively, desired α- and β-D-glucose esters.

According to this invention the above objects are accomplished by a process wherein 2,3,4,6-tetra-O-benzyl-D-glucopyranose (TBG) is metalated with n-butyllithium in either tetrahydrofuran (THF) or anhydrous benzene, and the metalated product acylated with an appropriate alkyl, alkenyl or aryl acid chloride to yield the 2,3,4,6-tetra-O-benzyl-1-O-acyl-D-glucopyranose esters (TBG esters). When the acyl group is saturated, the TBG ester is hydrogenated to yield the appropriate 1-α- or 1-β-D-glucose ester. Masking of the double bond or other appropriate techniques may be used to prepare the glucosyl esters if the acyl group in the TBG ester is unsaturated. When the reaction is run in THF the predominant product has the 1-α-configuration and when it is run in anhydrous benzene the predominant product has the 1-β-configuration.

DETAILED DESCRIPTION OF THE INVENTION

The α- and β-TBG esters and their hydrogenated products, α- and β-D-glucose esters, I and II, are prepared in high yield (85–90%) by the process of this invention:

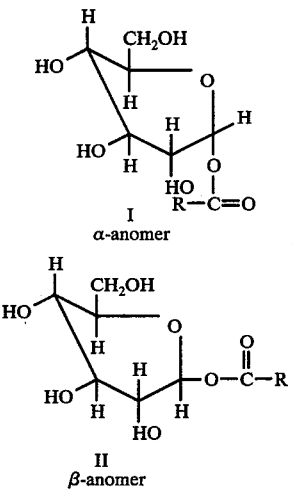

In both the glucose esters I and II and in the TBG esters (see IVa and b, that follow) R represents the appropriate ester group such as hexadecanoate, benzoate, acetate, cis-9,10-octadecenoate, octadecanoate, mesitoate, cis,cis-9,12-octadecadenoate, and cis, cis,cis-9,12,15-octadecatrienoate.

The stereochemistry of 1-O-acylation of appropriately protected D-glucose is controlled to produce, selectively, the α- and β-TBG esters and the α- and β-D-glucose esters represented above. Metalation of 2,3,4,6-tetra-O-benzyl-D-glucopyranose (III) in THF at −30° to −40° C using 1.1 equivalent of n-butyllithium (1.6 M in hexane) followed by acylation of the lithium salt of TBG with an appropriate acid chloride, such as hexadecanoyl chloride, produces a mixture of α- and β-D-anomeric esters IVa and IVb in a ratio of 9:1, respectively, in chromatographically purified yields exceeding 95%.

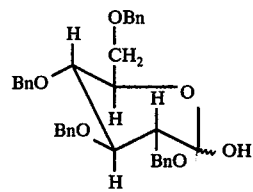

III

-continued

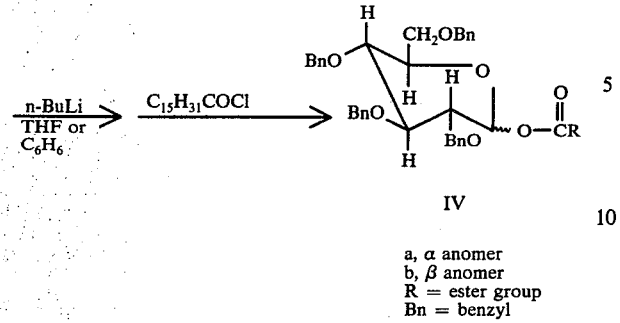

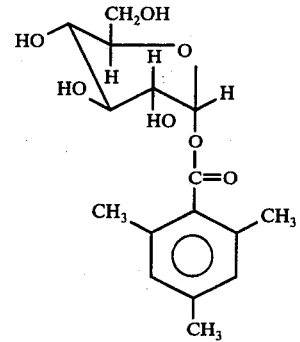

IV a, α anomer
b, β anomer
R = ester group
Bn = benzyl

When the esters are oils that cannot be crystallized, the anomeric composition is easily determined by evaluation of the proton nmr spectrum of the characteristic anomeric hydrogens. The physical properties of some TBG esters prepared by this process are shown in Table I. The benzyl group is easily removed from the acyl glucopyranose benzyl ester by well established hydrogenolysis, especially when the acyl group is saturated, to produce a quantitative yield of the desired 1-α- or 1-β-glucosyl ester.

Metalation of TBG with n-butyllithium in anhydrous benzene at about 60° C followed by acylation of the lithium salt of TBG with an appropriate acid chloride, such as hexadecanoyl chloride, produces a mixture of α- and β-D-anomeric esters IVa and IVb in a ratio of about 1:8, respectively. The physical properties of some TBG esters prepared by acylation in benzene are shown in Table II. As with the reaction in THF, the benzyl groups are removed by hydrogenolysis.

As shown in Table III, with THF as the solvent, increasing the acylation temperature diminishes selectivity for the α-anomer. Although the α:β ratio is altered, the α-D-anomer, IVa, still predominates, e.g., at temperature from 25°–60° C, the ratio is 2-2.5:1. In determining the parameters which influence the stereochemical course of the process of this invention, we discovered that a dramatic inversion in product ratio could be effected by changing the reaction medium. Thus, reaction of 2,3,4,6-tetra-O-benzyl-D-glucopyranose (III) in benzene at 62° C produces a 1:8 ratio of the α- and β-anomers, IVa and IVb, respectively. Compound IVb, mp 52°–53° C, $[\alpha]^{25}D + 9.1°$(c 1.0, $CH_2Cl_2$), is isolated from the reaction mixture by crystallization from absolute ethanol. At lower reaction temperatures, intermediate ratios of the α- and β-anomers are obtained; however, as shown in Table III, IVb predominates at temperatures above 5° C. Addition of 4% of a highly polar aprotic solvent, hexamethyl phosphoramide (HMPA), reverses the product distribution in benzene at 62° C to give the same product distribution observed in THF at temperatures from 25° to 60° C.

The process of this invention is the first single pathway to pure 1-α- and 1-β-D-anomeric esters and the first general, highyield route to pure unrearranged aliphatic 1-O-acyl-α-D-glucopyranose (I). It is the first method for preparing 1-α-D-glucosyl esters where the carboxylic acid group is not of a highly hindered nature such as mesitoyl (V) and galloyl (VI). As previously

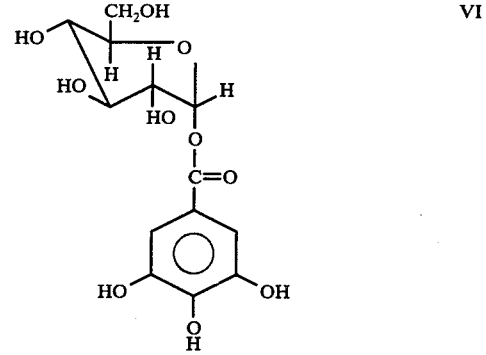

noted, these two compounds had to be made by indirect routes in low yields of 17% and 5%, respectively. Such hindered examples were previously chosen for the preparation of 1-α-glucosyl esters because the hindered ester functions are less likely to rearrange, that is, migrate from position 1 to position 2, under the non-neutral deblocking conditions utilized. The process of this invention employs a neutral deblocking procedure, hydrogenolysis, to yield pure 1-α-D-glucosyl esters derived from non-hindered alphatic and aromatic carboxylic acids in near quantitative yield without any rearrangement.

Since it is well established that TBG is in the α-configuration, one skilled in the art would expect that the acylation would always proceed to yield predominantly the α-anomeric ester of TBG. Consequently, we were surprised to discover that the lithium salt of TBG reacts with acid chloride to give either 1-α- or 1-β-ester, predominantly, depending on the solvent medium used to conduct the reaction. As previously noted, temperature also has some effect on the isomeric distribution of the product.

For the maximum yield of the 1-α-ester of TBG, the following reaction conditions are used: THF as solvent, a temperature of about −30° to −40° C, and a ratio of the lithium salt of TBG to acid chloride of about 1:1. For maximum yield of the 1-β-ester of TBG, the following reaction conditions are used: anhydrous benzene as solvent, a temperature of from about 45° to about 60° C, and a ratio of lithium salt of TBG to acid chloride of about 1:1. As shown in Table I, other reaction conditions may be used, but at a sacrifice in the yield of desired anomeric ester.

In addition to a report that several D-glucosyl fatty acid esters are active as plant growth regulating compounds [Chem. Ind. (London), 930 (1972)], other uses have been known for many years. For example, sugar esters (tallowates) have been used in detergent compositions (U.S. Pat. No. 2,970,962), as antispattering emulsifiers for shortenings and margarines (U.S. Pat. No. 1,917,257), in confectionary coatings (U.S. Pat. No. 2,999,023), in lubricating oils (U.S. Pat. No. 2,700,022), and in germicides (Mfg. Chem. 1958, 1948). Other utilities such as sludge inhibitors, pour point depressants, tablet coatings, plasticizers and food antioxidants are discussed in Sugar Esters, Preparation and Application, J. C. Colbert, Noyes Data Corp., Park Ridge, New Jersey and London, England, 1974.

The invention is exemplified as follows using the hexadecanoyl ester as a representative example:

Preparation of 2,3,4,6-Tetra-O-benzyl-1-hexadecanoyl-α-D-Glucopyranose

Into a dry 250-ml three-neck flask, flushed with $N_2$, was placed 125 ml of freshly distilled anhydrous THF and 5.40 g (0.010 mol) of dry 2,3,4,6-tetra-O-benzyl-D-glucopyranose (TBG). The solution was magnetically stirred and the TBG was thoroughly dissolved within a few minutes at room temperature. The solution was then cooled to $-30°$ to $-40°$ C and 6.8 ml (0.011 mol) of 1.6 M n-butyllithium in hexane was added. The homogeneous reaction mixture was stirred at this temperature for 3 min whereupon 3.0 g (0.011 mol) of hexadecanoyl chloride was added and the reaction continued for 20 min. The reaction was then allowed to warm to room temperature, quenched with a saturated solution of ammonium chloride, and extracted with methylene chloride. The methylene chloride extracts were dried over sodium sulfate and the solvent removed to yield 7.8 g of crude ester (100%). The crude ester was eluted through an 18 × 0.75 in. column of Florisil (a synthetic magnesium silicate adsorbent, 100 mesh/200 mesh) with 50:50 methylene chloride-petroleum ether to give 7.7 g (97%) of a glassy solid. Attempts to crystallize this material failed. $^1$H NMR in CDCl$_3$ showed the characteristic α and β anomeric proton resonances at δ 6.65 (d, J = 2.62 Hz) and 5.85 (d, J = 6.75 Hz) in the ratio of 9:1, respectively. The ratio of the sum of the α and β anomeric proton resonances to the 2-position methylene resonances of the aliphatic chain at δ 2.5 was 1:2, indicating monoesterification. Ir (neat film) C=O, 1745 cm$^{-1}$; $[\alpha]^{25}$D + 45.9° (c 1.0, CH$_2$Cl$_2$).

Preparation of 2,3,4,6-Tetra-O-benzyl-1-hexadecanoyl-β-D-glucopyranose

The preparation of the β-anomeric ester was similar to the above except that the reaction was carried out in an anhydrous benzene. Metalation and solubilization of the TBG was carried out at 0° C. Acylation was then effected at 62° C for 20 min. Workup was essentially the same as above. Examination of the reaction mixture before crystallization by $^1$H NMR indicated a ratio of α:β anomers or 11:89. The yield of crude ester was 95%. Crystallization of the product from absolute ethanol gave pure β anomer, mp 52°-53° C, in 85% yield. $^1$H NMR in CDCl$_3$ showed the characteristic β-anomeric proton resonance at δ 5.85 (1 H,d,J = 6.75 Hz), 2.5 (2 H,t,J = 6.75 Hz, the 2 position CH$_2$ of the fatty acid chain); ir (neat film) C=O 1750 cm$^{-1}$; $[\alpha]^{25}$D + 9.1° (c 1.0, CH$_2$Cl$_2$).

Hydrogenolysis of IVa and IVb

IVa (90% α and 10% β) or compound IVb (100% β) (2 g, 0.00025 mol) were dissolved in 20 ml of absolute ethanol containing 75 mg of Pd black. The solutions were shaken on a Parr hydrogenator at room temperature for 8 h at 40 psi. The ester I in which R is n-C$_{15}$H$_{31}$ crystallized out of solution following hydrogenolysis of IVa in 92% yield. Recrystallization from CHCl$_3$ gave a solid which rearranged on melting, mp 98°-108° C, $[\alpha]^{25}$D + 66.9° (c 0.9, MeOH). $^1$H NMR (CD$_3$OD), taken at 60° C in a sealed tube because of the compounds' insolubility, showed resonances at δ 6.45 (1H,d,J = 3.0 Hz, anomeric proton), 2.50 (2 H,t,J = 6.75 Hz, 2-position CH$_2$ protons of the aliphatic chain); ir (KBr pellet) C=O at 1740 cm$^{-1}$.

The ester II in which R is also n-C$_{15}$H$_{31}$ was isolated in 96% yield after recrystallization from ethyl acetate: mp 108, 170°-175° C (double melting point); $[\alpha]^{25}$D −1.17° (c 1.2, MeOH); $^1$H NMR (CD$_3$OD) at 60° C δ, 5.62 (1 H,d,J = 6.75 Hz, anomeric proton), 2.50 (2 H,t,J = 6.75 Hz, 2-position CH$_2$ protons of the aliphatic chain); ir (KBr pellet) shows three C=O peaks at 1760, 1750, and 1740 cm$^{-1}$.

The isomeric purity of the hexadecanoates and I and II was confirmed by GLC analysis of the corresponding Me$_4$Si derivatives. Separation of these was made on a 6 ft × 0.25 in. glass column packed with 3% SP 2100 (OV-1 silicone coated gas-chromatographic column) and programmed from 180° to 250° C, 6° C/min. Under these conditions the hexadecanoates I and II have retention times of 12.0 and 12.5 min, respectively.

Other 1-α- and 1-β-D-glucosyl and TBG esters, such as the benzoate, and acetate, mesitoate, octadecanoate, cis-9,10-octadecenoate, cis,cis-9,12-octadecadienoate, and cis,cis,cis-9,12,15-octadecatrienoate, were made by the same process.

TABLE 1

| Acylation Products of TBG$^-$Li$^+$ in THF at −30 to −40° C$^a$ | | | | |
|---|---|---|---|---|
| | | δ (ppm) C$_1$-H,J (Hz) | | |
| R | ir, C=O, cm$^{-1}$ | α-anomer | β-anomer | $[\alpha]_D^{25}$ (CH$_2$Cl$_2$, 1c) |
| C$_{17}$H$_{35}$$^b$ | 1745$^c$ | 6.65(d,2.6) | 5.85(d,6.8) | +39.2 |
| C$_{15}$H$_{31}$$^b$ | 1745$^c$ | 6.65(d,2.6) | 5.85(d,6.8) | +45.9 |
| cis-9,C$_{17}$H$_{33}$$^b$ | 1750$^c$ | 6.65(d,2.6) | 5.85(d,6.8) | +42.8 |
| phenyl$^d$ | 1740$^e$ | 6.70(d,3.3) | 5.90(m)$^f$ | +73.5 |
| p-nitrophenyl$^g$ | 1737$^e$ | 6.60(d,3.3) | 5.90(m)$^f$ | +72.0 |
| 2,4,6-trimethylphenyl | 1740$^e$ | 6.66(d,2.7) | 5.90(m)$^f$ | +73.7 |

$^a$All products are 90% α-anomer, 10% β except where otherwise indicated, rotations are for pure α-anomers when recrystallization was possible.
$^b$Noncrystallizable glasses.
$^c$Neat films.
$^d$mp of recrystallized product 84–85° C (EtOH).
$^e$Chloroform solution.
$^f$ABX multiplet.
$^g$mp of recrystallized product 124.2–125.0° C (EtOH).

TABLE II

Acylation Products of TBG⁻Li⁺ in Benzene at 60° [a]

| R | ir, C=O, cm$^{-1}$ | δ (ppm) C$_1$-H, J (Hz) α-anomer | δ (ppm) C$_1$-H, J (Hz) β-anomer | $[α]_d^{25}$ (CH$_2$Cl$_2$, 1c) |
|---|---|---|---|---|
| C$_{17}$H$_{35}$[b] | 1750 | 6.65(d,2.6) | 5.85(d,6.8) | +10.7 |
| C$_{15}$H$_{31}$[c] | 1750 | 6.65(d,2.6) | 5.85(d,6.8) | + 9.1 |
| phenyl[d] | 1735 | 6.70(d,3.3) | 5.90(m)[e] | −23.0 |
| 2,4,6-trimethylphenyl[f] | 1740 | 6.66(d,2.8) | 5.90(m)[d] | + 1.6 |
| p-nitrophenyl[g] | 1737 | 6.60(d,3.3) | 5.90(m)[d] | −27.0[h] |

[a] All products were 90% β, 10% α, rotations are for pure β-anomers when recrystallization was possible.
[b] Noncrystallizable glass.
[c] mp of recrystallized product 52–53° C (EtOH).
[d] mp of recrystallized product 96.0–97.2° C (cyclohexane).
[e] ABX multiplet.
[f] mp of recrystallized product 131.0–131.5° C (EtOH).
[g] mp of recrystallized product 96–98° C.
[h] (Dioxane, 6 c).

TABLE III

Stereochemical Distribution of Anomeric 1-0-Hexadecanoyl-D-TBG as a Function of Temperature and Solvent

| Solvent | α | β | Temperature (° C) | $[α]_D^{25}$ (CH$_2$Cl$_2$, 1c) |
|---|---|---|---|---|
| THF | 90% | 10% (via nmr)[a] | −30 to −40° | +45.9 |
| " | 70 | 30 | 25° | +39.2 |
| " | 70 | 30 | 45° | — |
| " | 70 | 30 | 60° | +36.0 |
| Benzene | 50 | 50 | 0 to 5° | +27.8 |
| " | 26 | 74 | 40 to 45° | +20.6 |
| " | 11 | 89 | 62° | +14.9 |
| Benzene + 4% HMPA | 70 | 30 | 62° | +35.0 |

[a] Derived from the integration of the anomeric protons.

We claim:

1. A process for the preparation of anomerically pure 1-α- and 1-β-D-glucosyl esters comprising metalating 2,3,4,6-tetra-O-benzyl-D-glucopyranose with n-butyllithium in a solvent selected from the group consisting of tetrahydrofuran and anhydrous benzene, acylating the metalated product with an appropriate acid chloride, and hydrogenating the resultant acyl glucopyranose.

2. The process of claim 1 wherein the reaction is conducted at a temperature of from about −30° C to about −40° C and the ratio of the lithium salt of 2,3,4,6-tetra-O-benzyl-D-glucopyranose to acid chloride is about 1:1.

3. The process of claim 2 wherein the acid chloride is selected from the group consisting of benzoyl chloride, acetoyl chloride, cis-9,10-octadecenoyl chloride, hexadecanoyl chloride, octadecanoyl chloride, mesitoyl chloride, cis,cis-9,12-octadecadienoyl chloride, and cis,cis,cis-9,12,15-octadecatrienoyl chloride.

4. The process of claim 1 wherein the reaction is conducted at a temperature of about 60° C and the ratio of the lithium salt of 2,3,4,6-tetra-O-benzyl-D-glucopyranose to acid chloride is about 1:1.

5. The process of claim 4 wherein the acid chloride is selected from the group consisting of benzoyl chloride, acetoyl chloride, hexadecanoyl chloride, cis-9,10-octadecenoyl chloride, octadecanoyl chloride, mesitoyl chloride, cis,cis-9,12-octadecadienoyl chloride, and cis,cis,cis-9,12,15-octadecatrienoyl chloride.

* * * * *